United States Patent [19]

Fischer et al.

[11] Patent Number: 5,002,489
[45] Date of Patent: Mar. 26, 1991

[54] DENTAL PROSTHESIS

[75] Inventors: Artur Fischer, Waldachtal/Tumlingen; H. Weber, Tübingen; Günter Rübeling, Bremerhaven, all of Fed. Rep. of Germany

[73] Assignee: fischerwerke Artur Fischer GmbH & Co. KG, Tumlingen/Waldachtal, Fed. Rep. of Germany

[21] Appl. No.: 300,062

[22] Filed: Jan. 23, 1989

[30] Foreign Application Priority Data

Jan. 23, 1988 [DE] Fed. Rep. of Germany ....... 3801994

[51] Int. Cl.$^5$ .............................................. A61C 5/08
[52] U.S. Cl. .................................... 433/218; 433/219; 433/209
[58] Field of Search ............... 433/181, 182, 183, 223, 433/219, 209, 210, 218

[56] References Cited

U.S. PATENT DOCUMENTS

| | | | |
|---|---|---|---|
| 1,008,028 | 11/1911 | Gollobin et al. | 433/172 |
| 1,218,033 | 3/1917 | Yirikian | 433/181 |
| 1,364,770 | 10/1921 | Yirikian | 433/181 |
| 1,417,376 | 5/1922 | Greenberg | 433/181 |
| 1,520,809 | 12/1924 | Cohen | 433/181 |
| 1,577,753 | 3/1926 | Rafkin | 433/209 |
| 4,627,136 | 12/1986 | Kreylos et al. | 433/218 |
| 4,681,542 | 7/1987 | Baum | 433/219 |
| 4,789,338 | 12/1988 | Eisenmann | 433/181 |

FOREIGN PATENT DOCUMENTS

| | | | |
|---|---|---|---|
| 339419 | 7/1921 | Fed. Rep. of Germany | 433/204 |
| 841188 | 6/1952 | Fed. Rep. of Germany | |
| 2812175 | 9/1979 | Fed. Rep. of Germany | 433/174 |
| 2920112 | 11/1980 | Fed. Rep. of Germany | |
| 2945489 | 3/1986 | Fed. Rep. of Germany | |
| 3526976 | 1/1987 | Fed. Rep. of Germany | |
| 639551 | 11/1983 | Switzerland | |

OTHER PUBLICATIONS

German Patent Office Search Report dated Jun. 29, 1988 concerning the corresponding West German Patent Application Ser. No. P 38 01 994.9 (3 pages).
Themann, Jan Dirk: "Gute Ideen helfen sparen eine Madenschraube sorgt für Friktion", *Dental-Labor*, XXXV, Heft 2/87, 201 (2 pages).
Wupper, Hans: "Geschiebeverankerung oder Teleskopverankerung?", *Dental-Labor*, XXXI, Heft 5/83, 603 (6 pages).
"Zwei neue Hafner-Hilfsteile für die Präzisionstechnik", *Dental Echo*, 1968, p. 185.
VDI-Richtlinien, VDI 3402 Blatt 1, Mar. 1976, 4 pages.

Primary Examiner—Cary E. Stone
Attorney, Agent, or Firm—Michael J. Striker

[57] ABSTRACT

A dental prosthesis comprises an element fixed in a mouth, a removable dental porsthesis component placed on the element, and a removable connection of the dental prosthesis component with the element and including vertical groove formed in an adjacent surface in each of the element and the component, the grooves being located immediately opposite to one another and open into one another, the connection further including a resilient friction element engaging in the grooves.

17 Claims, 5 Drawing Sheets

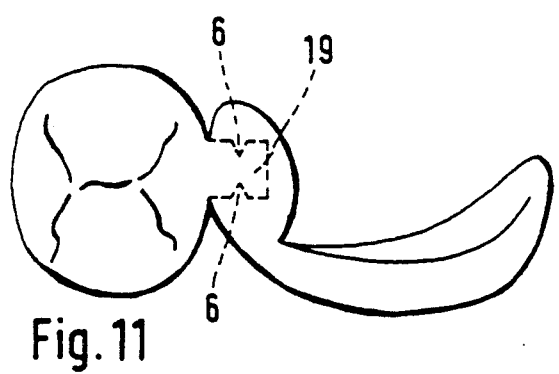
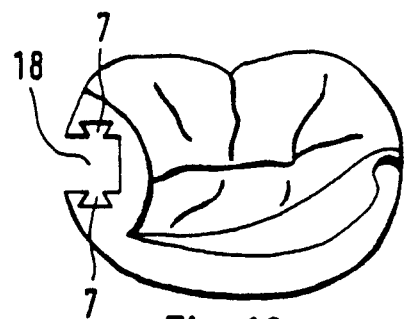
Fig. 11   Fig. 12
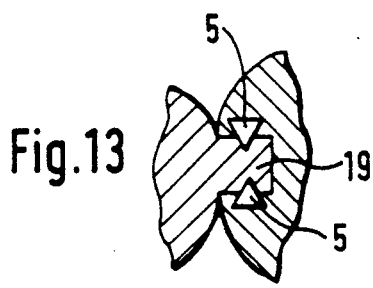
Fig. 13
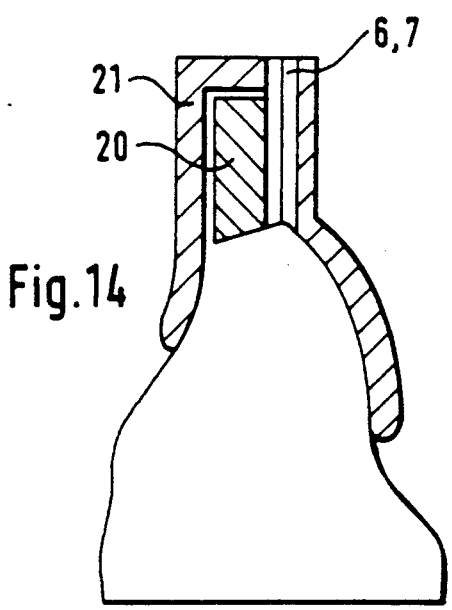
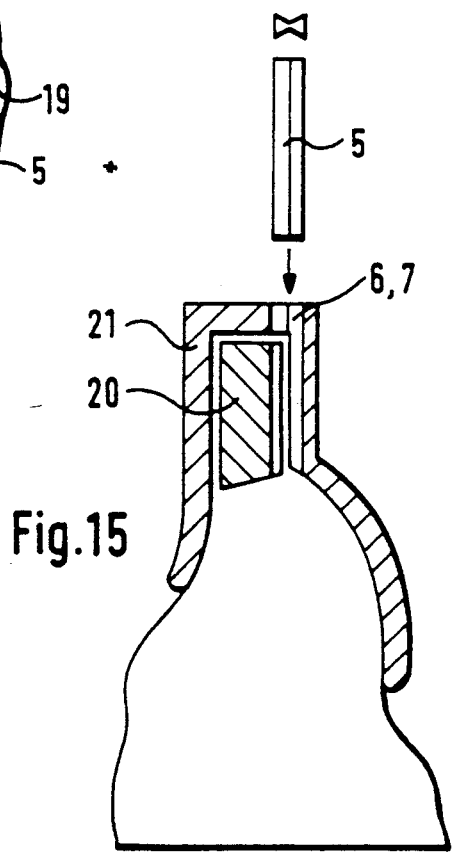
Fig. 14   Fig. 15
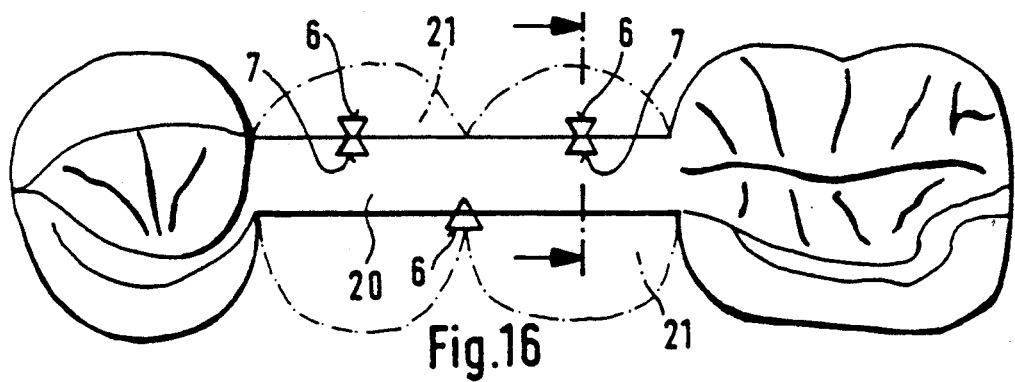
Fig. 16

DENTAL PROSTHESIS

BACKGROUND OF THE INVENTION

The present invention relates to a dental prosthesis. More particularly it relates to such dental prosthesis which has a frictional connection between an element fixed in a mouth and a removable component.

It is known to use for dental prosthesis the detachable connections which are customarily formed as metal push-fit members The metal-based push-fit members must be soldered, welded or cast on. The fitting of the push-fit members requires considerable time expenditure, and the use of the metal push-fit members increases the variety of alloys in the mouth increasing the risk of electrochemical reaction which is accompanied by a local tissue reactions or allergies. In addition the loss of friction occurring during the use of metal push-fit members/telescopes is frequently a problem which can be solved only with great financial expenses, if at all.

The German document DE-OS 3,540,049 discloses a push-fit connection in which the connection between the male component and the female component is produced by a hardenable synthetic plastic material which is subsequently introduced. The push-fit component can be made of course with correspondingly sized tolerances, however the subsequent introduction of the hardenable synthetic plastic material presents problems This known push-fit connection requires a large amount of space, which also limits its possible uses. In addition, the required permanent bond between plastic material and metal is not sufficiently insured.

SUMMARY OF THE INVENTION

Accordingly, it is an object of the present invention to provide a dental prosthesis having a frictional connection, in which the connection takes as little space as possible and is economical to produce.

In keeping with these objects and with others which will become apparent hereinafter, one feature of the present invention resides, briefly stated, in a dental prosthesis in which a vertical groove is formed in adjacent surfaces of an element fixed in a mouth and a removable component fitting over the element fixed in the mouth so that the grooves are located directly opposite to one another, and the resilient friction element engages in both grooves.

In accordance with the present invention the grooves in which the resilient friction element is inserted are produced in the outer surface of the primary element which is fixed in the mouth such as a telescope crown or internal telescope, and on the inner surface of the removable components such as a removable crown or external telescope. The friction element is pressed into the grooves so that the friction between the friction element and the inner surface of the groove is sufficient to fix the dental prosthesis securely in the mouth. However, the friction in the grooves is not too great for removal of the dental prosthesis.

The friction element which is used in accordance with the present invention is preferably a profile pin composed of polyamide and engaging the undercuts in the grooves with its x-shaped profile. The cross-section of such profile can be for example curved, swallow-tailed or triangular.

In accordance with another feature of the present invention the grooves which are located opposite to one another do not have the same cross-sectional shape. For example, one groove can be trapezoidal, while the other groove in the opposite surface can be semi-circular. The semi-circular groove in this case can be provided on the outer surface of the inner telescope crown, while the trapezoidal groove can be provided on the inner surface of the outer removable crown. The profile pin in all embodiments of the invention is positively secured in the outer removable crown.

In accordance with a further feature of the present invention, the length of the groove in the outer removable crown of the dental prosthesis component is greater than the length of the groove in the inner telescope crown located on the tooth stump.

For producing the groove for the frictional connection in accordance with the present invention a spark erosion can be used. Correspondingly profiled electrodes can be displaced so as to produce the grooves in the inner telescope crown and in the outer removable crown fitted thereon. During this operation the crowns are arranged in the intended position on a model of the jaw for insuring extremely accurate arrangement of the grooves and a correspondingly accurate connection thereafter. Then the friction element is pushed into the grooves and its projecting end is cut off. When the dental prosthesis is removed the friction element remains as a male component in the dental prosthesis.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 8-20 are views showing further embodiments of the present invention.

DESCRIPTION OF THE PREFERRED EMBODIMENTS

Figure 1:
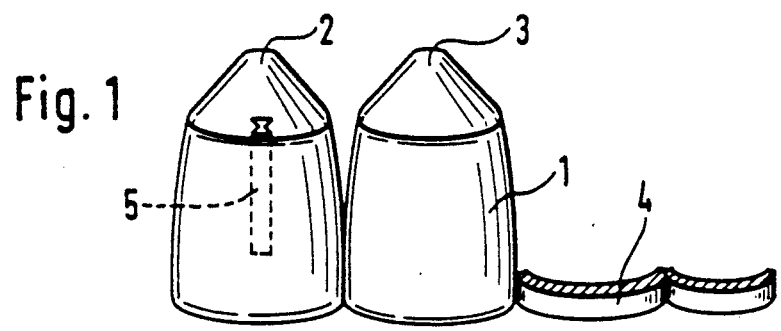
FIG. 1 is a view showing a part of a dental prosthesis in accordance with the present invention.

A dental prosthesis component 1 shown in FIG. 1 has two crowns 2 and 3 which are connected with one another and a yoke 4 extending to other not shown crowns.

Figure 2:
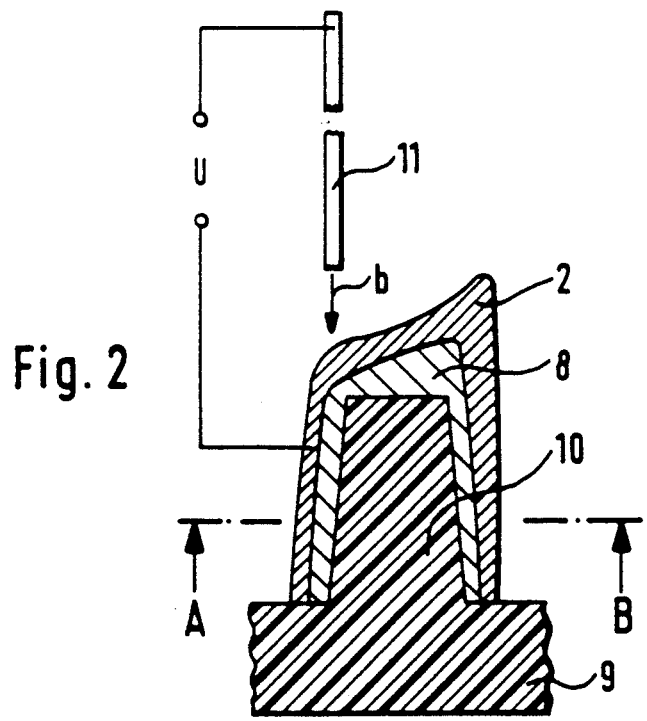
FIG. 2 is a view illustrating the making of a groove in an inner telescope crown and in an outer removable crown of a dental prosthesis component in accordance with the present invention.

As can be seen from FIG. 2, the removable crown 2 of the dental prosthesis component 1 is fitted on a fixed inner telescope crown 8. The latter is placed on a tooth stump 10 of a jawbone 9 of a model of a tooth. Resilient friction element 5 connects the removable crown 2 with the inner fixed telescope crown 8.

Connection between the crown 2 and telescope crown 8 is performed by resilient friction element 5. This element engages in correspondingly profiled grooves in the crown 2 and the telecope crown 8. As can be seen from FIG. 3, the crown 2 is provided with a groove 6, while the telescope crown 8 is provided with a groove 7, and the grooves are arranged directly opposite to one another. The groove 6 has an undercut in the crown 2, while the groove 7 has a corresponding undercut in the telescope crown 8.

For making the above mentioned grooves 6 and 8 an electrode 11 profiled in correspondence with the shape of the grooves 6 and 7 is displaced downwardly in direction of the arrow b and produces the grooves with the use of spark erosion. The voltage U which is required for this operation is applied between the electrode 1 and the metal crowns 2 and 8 by a spot-erosion generator. When the electrode 1 is moved down in direction of the arrow b, a groove corresponding to the profiled electrode 11 is produced in the region of the contacting surfaces of the removable crown 2 and the telescope crown 8. The profile which includes the grooves 6 and 7 formed in the contact surfaces as shown in FIG. 3 can be produced by using an electrode of a triangular cross-section and using the spark-erosion process twice.

When the grooves 6 and 7 are made, the resilient friction element 5 is inserted in the thus formed double groove 6, 7 from above in direction of the arrow b. The friction element can be preferably formed as a polyamide profile rod. The profile of the profile rod 5 shown in FIG. 1 is matched to the profile of the combined groove 6, 7 so that a frictional connection is established between the profile rod 5 and all of the grooves 6 and the groove 7. Then the inserted profile rod 5 is cut off flush at the top. It is not necessary to provide an additional securing of the profile rod 5 since it is held in the groove 6 by the frictional force.

For remaining the profile rod 5 in the dental prosthesis component 1 when it is removed, the frictional force between the profile rod 5 and the wall of the groove 6 should be greater than the frictional force between the profile rod 5 and the wall of the groove 7. This can be achieved by providing a greater pressure between the profile rod 5 and the removable crown 12 in the region of the groove 6 then in the groove 7. For this purpose the length of the groove 6 in the outer removable crown of the dental prosthesis component can be greater than the length of the groove 7 in the inner telescope crown located on the tooth stump, as shown in FIG. 3a.

Figure 3:
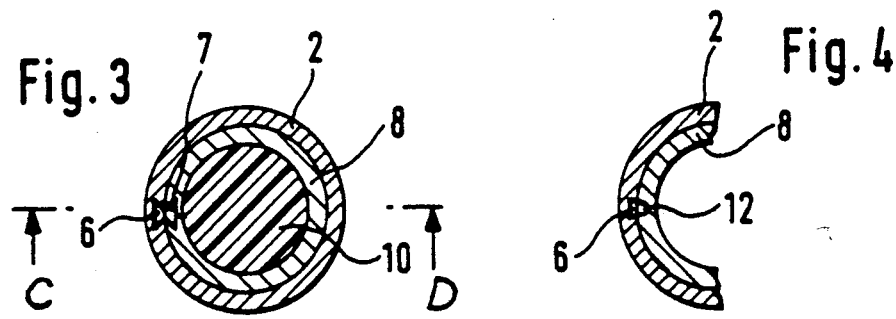
FIG. 3 is a view showing a cross-section taken along the line A-B in FIG. 2 after the producing of the grooves.
Figure 3A:
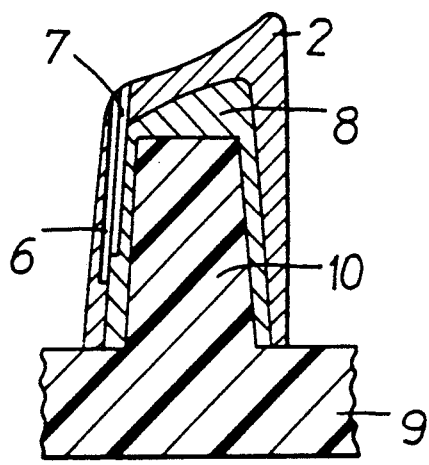
FIG. 3a is a view showing a longitudinal cross-section taken along the line C-D in FIG. 3.

The double groove 6, 7 shown in FIG. 3 is shaped so that it is suitable for accommodating the profile rod 5 of FIG. 1.

Figure 4:
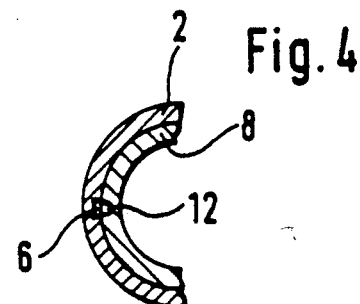
FIG. 4 is a view showing a partial cross-section of FIG. 2 with grooves having different profiles.

FIG. 4 shows a double groove in accordance with another embodiment of the present invention. The double groove includes the undercut groove 6 in the crown 2 and a rounded groove 12 in the telescope crown 8. The double groove 6, 12 has an approximately triangular cross-section. Because of the friction between the correspondingly profiled profile rod and the telescope crown 8 it can produce a completely satisfactory holding values for the dental prosthesis component. The triangular double groove is especially easy to handle.

It should be emphasized that the position of the grooves can be selected to suit individual requirements due to their small dimensions The grooves can be arranged interdentally, laterally or at the side of the dental prosthesis component facing the mouth cavity. High holding values may be achieved when required by making two double grooves in a single crown.

Figure 5:
FIGS. 5-7 are views showing various embodiments of profile pins for inserting into corresponding profiled grooves.
Figure 5:
Figure 5:
Figure 5:
Figure 6:
Figure 7:
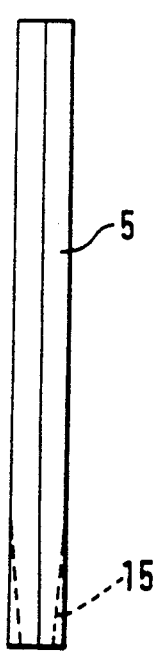

Profile pins 13, 14, 5 are shown in side view and in profile in FIGS. 5–7. As can be seen from FIG. 7, the profile pin 5 can be tapered slightly conically at its lower end shown by a broken line 15. Such a conical tapering can facilitate the introduction of the profile pin 5 into the double groove 6, 7.

The embodiments of the different profile shapes shown in the drawings can be modified in accordance with the requirements, depending on the particular application. The same is true for the cross-sectional shapes of the electrodes which are used for producing the desired groove profiles by spark erosion.

Figure 8:
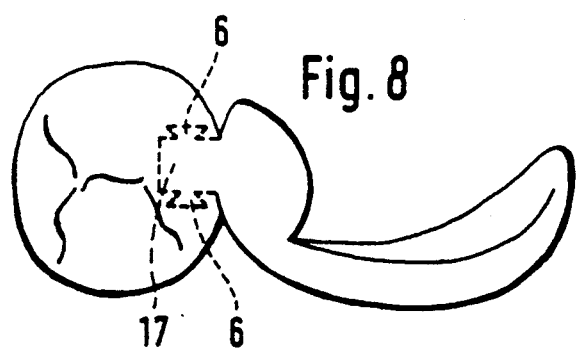
Figure 9:
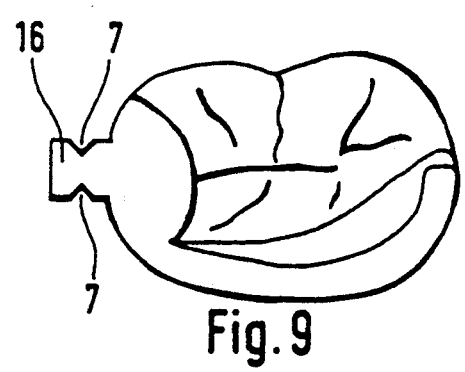
Figure 10:
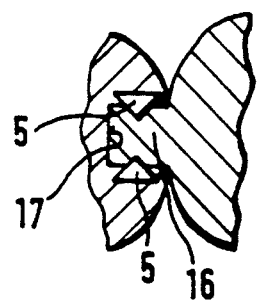

FIGS. 8–20 show further embodiments of the present invention. FIGS. 8–10 show a dental prosthesis in which a bridge fixed in a mouth has a block 16 formed integrally with it. It engages in a corresponding recess 17 in a removable dental prosthesis component. The connection between the adjacent surfaces is provided by means of the friction elements 5 which engage in the corresponding grooves 6, 7.

FIGS. 11–13 show a substantially similar embodiment. In this case, however, a block 19 is attached to the removable dental prosthesis component. The bridge is provided with a recess 18 in which the block 19 engages.

FIGS. 14–16 show an embodiment which has a horizontal bar 20 while a removable dental prosthesis component 21 fits over the bar. The grooves 6, 7 are provided between the bar 20 and the dental prosthesis component 21, and the corresponding friction elements engage in the groove. The resilient friction elements are firmly connected to the removable dental prosthesis component 21. However, if necessary, the friction elements can still be replaced.

Figure 17:
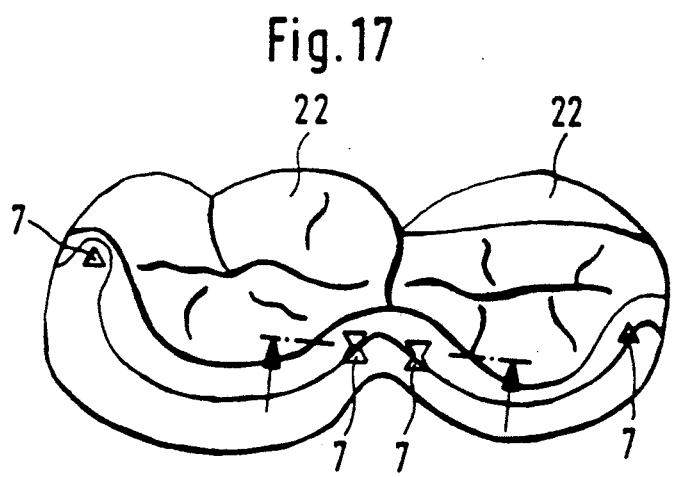
Figure 19:
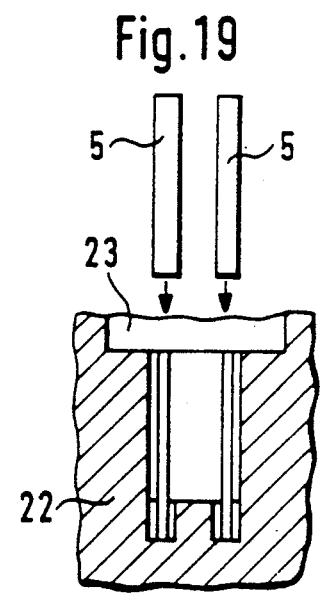
Figure 18:
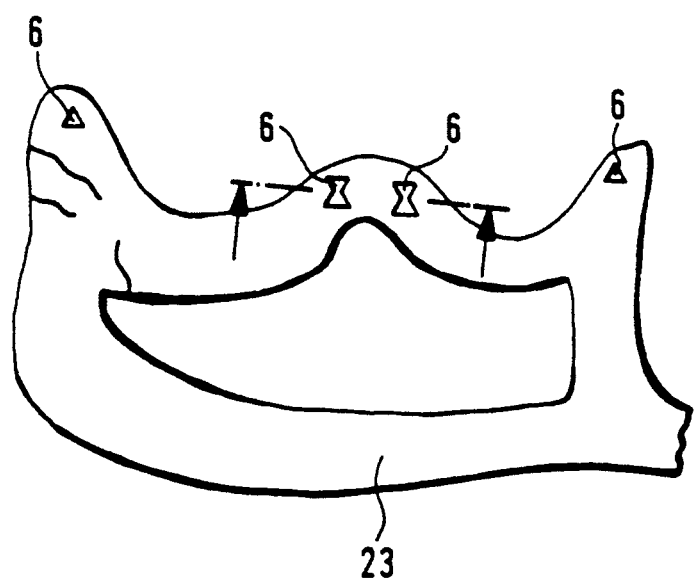
Figure 20:
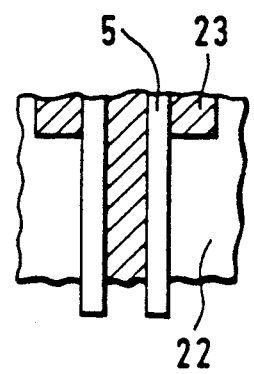

FIGS. 17 shows a primary component 22 with two adjacent crowns and a secondary component 23 shown partially in FIG. 18 anchored to the same. The secondary component 23 forms the removable component of the dental prosthesis. FIGS. 19 and 20 show the arrangement of the resilient friction elements 5 which engage in the grooves 6, 7.

It will be understood that each of the elements described above, or two or more together, may also find a useful application in other types of constructions differing from the types described above.

While the invention has been illustrated and described as embodied in a dental prosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims

We claim:

1. A dental prosthesis, comprising an element fixed in a mouth; a removable dental prosthesis component placed on said element; and means for removably connecting said dental prosthesis component with said element and including vertical grooves formed in an adjacent surface in each of said element and said component, said grooves being located immediately opposite to one another and open into one another, said means further including a resilient friction element engaging in said grooves, said groove in said removable dental prosthesis having a length which is greater than the length of said groove in said element.

2. A dental prosthesis as defined in claim 1, wherein said element fixed in a mouth is a telescope crown.

3. A dental prosthesis as defined in claim 1, wherein said element fixed in a mouth is a bridge.

4. A dental prosthesis as defined in claim 1, wherein said dental prosthesis component is a removable crown.

5. A dental prosthesis as defined in claim 1, wherein said removable dental prosthesis component includes a push-fit member, said grooves being formed in adjacent surfaces of said element and said push-fit member.

6. A dental prosthesis as defined in claim 1, wherein said profile pin is formed as a polyamide profile pin.

7. A dental prosthesis as defined in claim 1, wherein said grooves of said means have cross-sections with different shapes.

8. A dental prosthesis as defined in claim 1, wherein said grooves of said means have cross-sections with identical shapes.

9. A dental prosthesis as defined in claim 1, wherein said grooves have a trapezoidal cross-section.

10. A dental prosthesis as defined in claim 1, wherein said grooves have a triangular cross-section.

11. A dental prosthesis as defined in claim 1, wherein said grooves have a semi-circular cross-section.

12. A dental prosthesis as defined in claim 1, wherein said grooves have a swallow-tailed cross-section.

13. A dental prosthesis as defined in claim 1, wherein said groove in said removable dental prosthesis has a length which is greater than a length of said groove in said element.

14. A dental prosthesis as defined in claim 1; and further comprising a push-fit member formed as a square block and a corresponding recess in said removable dental prosthesis component fitting around said block, said grooves being formed in walls of said block and said dental prosthesis component, said block and said recess having adjacent surfaces provided with said grooves.

15. A dental prosthesis as defined in claim 1; and further comprising a block formed integrally with said removable dental prosthesis component and a push-fit member provided with a square recess in which said block engages, said block and said recess having adjacent surfaces provided with said grooves.

16. A dental prosthesis as defined in claim 1, wherein said element is formed as a horizontal bar.

17. A dental prosthesis as defined in claim 1; and further comprising at least one second groove provided in each of said element and said removal dental prosthesis component and at least one second such resilient friction element engaged in said second groove.

* * * * *